United States Patent [19]

Navarrini et al.

[11] Patent Number: 5,498,682
[45] Date of Patent: Mar. 12, 1996

[54] PERFLUORODIOXOLES, THE PREPARATION PROCESS THEREOF, AND HOMOPOLYMERS AND COPOLYMERS OBTAINED THEREFROM

[75] Inventors: Walter Navarrini; Vito Tortelli; Pasqua Colaianna, all of Milan; Julio A. Abusleme, Saronno, all of Italy

[73] Assignee: Ausimont, S.p.A., Milan, Italy

[21] Appl. No.: 270,149

[22] Filed: Jul. 1, 1994

[30] Foreign Application Priority Data

Jul. 5, 1993 [IT] Italy .................. MI93A1445

[51] Int. Cl.⁶ .................. C08F 14/18
[52] U.S. Cl. .................. 526/247
[58] Field of Search .................. 526/247

[56] References Cited

U.S. PATENT DOCUMENTS

| | | |
|---|---|---|
| 2,946,763 | 7/1960 | Bro et al. . |
| 3,635,926 | 1/1972 | Gresham et al. . |
| 3,642,742 | 2/1972 | Carlson . |
| 3,865,845 | 2/1975 | Resnick . |
| 3,978,030 | 8/1976 | Resnick . |
| 4,029,868 | 6/1977 | Carlson . |
| 4,399,264 | 8/1983 | Squire .................. 526/247 |
| 4,485,250 | 11/1984 | Squire .................. 526/247 |
| 4,558,141 | 12/1985 | Squire . |
| 4,587,316 | 5/1986 | Nakagawa et al. . |
| 4,827,024 | 5/1989 | Guglielmo et al. . |
| 4,846,006 | 7/1989 | Thibeault . |
| 4,864,006 | 9/1989 | Thibeault . |
| 4,879,362 | 11/1989 | Morgan .................. 526/247 |
| 4,908,410 | 3/1990 | Malhotra .................. 526/247 |
| 4,920,170 | 4/1990 | Abe et al. .................. 526/247 |
| 5,102,965 | 4/1992 | Carlson .................. 526/247 |
| 5,145,925 | 9/1992 | Ihara et al. .................. 526/247 |
| 5,176,958 | 1/1993 | Shimizu et al. .................. 526/247 |
| 5,182,342 | 1/1993 | Feiring et al. . |
| 5,284,708 | 2/1994 | Shimizu et al. .................. 526/247 |
| 5,286,825 | 2/1994 | Anton et al. .................. 526/247 |

FOREIGN PATENT DOCUMENTS

| | | |
|---|---|---|
| 0073087 | 3/1983 | European Pat. Off. . |
| 0076581 | 4/1983 | European Pat. Off. . |
| 0080187 | 6/1983 | European Pat. Off. . |
| 0184459 | 6/1986 | European Pat. Off. . |
| 0185241 | 6/1986 | European Pat. Off. .......... 526/247 |
| 0247379 | 12/1987 | European Pat. Off. . |
| 0296559 | 12/1988 | European Pat. Off. .......... 526/247 |
| 0460946 | 12/1991 | European Pat. Off. . |
| 0499158 | 8/1992 | European Pat. Off. . |
| 61-87764 | 5/1986 | Japan .................. 526/247 |
| 1514700 | 6/1978 | United Kingdom . |
| WO91/03472 | 3/1991 | WIPO . |
| WO91/04251 | 4/1991 | WIPO . |

OTHER PUBLICATIONS

European Search Report dated Sep. 8, 1994 for EP 94 10 9782 with Annex.

*Primary Examiner*—Joseph L. Schofer
*Assistant Examiner*—N. Sarofim
*Attorney, Agent, or Firm*—Bryan Cave

[57] ABSTRACT

The invention relates to new thermoprocessable copolymers of tetrafluoroethylene constituted by perfluoromethylvinylether (0.5–13% by weight), a fluorinated dioxole (0.05–3%) and tetrafluoroethylene (difference to 100%), particularly useful for coating electric cables by melt extrusion. It relates also to new perfluorodioxoles of formula

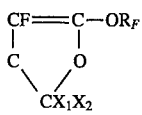

wherein $R_F$ is a $C_1$–$C_5$ perfluoroalkyl radical; $X_1$ and $X_2$ are, independently from each other, F or $CF_3$; and their homopolymers and copolymers, in particular thermoprocessable copolymers as defined above.

3 Claims, No Drawings

PERFLUORODIOXOLES, THE PREPARATION PROCESS THEREOF, AND HOMOPOLYMERS AND COPOLYMERS OBTAINED THEREFROM

The present invention relates to a new class of perfluorodioxoles, some processes for their preparation and the homopolymers and copolymers obtained from such perfluorodioxoles. It relates also to new thermoprocessable copolymers of tetrafluoroethylene containing fluorodioxoles, particularly suitable for coating electric cables by melt extrusion.

FEP copolymers (tetrafluoroethylene-hexafluoropropene copolymers) are known, having a melting temperature of about 260°–265° C. and endowed with relatively good mechanical properties up to a temperature of 200° C., as described for instance in U.S. Pat. No. 2,946,763. It is known that, for the processing of thermoprocessable polymers by extrusion, a low melt viscosity is required, i.e. a high melt flow index. A reduction of viscosity leads to a decay of the mechanical properties. To attenuate this effect, copolymers having a higher percentage of hexafluoropropene are prepared. However, the use of a higher percentage of this comonomer implies a sharp reduction of the melting point and therefore a lower rating temperature.

U.S. Pat. No. 4,029,868 illustrates another kind of FEP copolymers containing, besides tetrafluoroethylene and hexafluoropropene, from 0.5 to 3% by weight of a third monomer consisting of perfluoropropylvinylether or perfluoroethylvinylether. These terpolymers have a viscosity lower than the FEP copolymers containing only tetrafluoroethylene and hexafluoropropene.

Nevertheless, mechanical properties at high temperature (200° C.) remain still acceptable. According to the same patent above, perfluoromethylvinylether is not suitable as third monomer (see, in particular col. 3, lines 38–39 and comparative example A).

U.S. Pat. No. 4,587,316 suggests the use, as third monomer, of perfluoroalkylvinylethers wherein the perfluoroalkyl group contains an even higher number of carbon atoms: from 4 to 10.

Typically a FEP terpolymer containing about 6% by mols of hexafluoropropene and about 0.4% by moles of perfluoropropylvinylether and having a melt index of about 18–20 shows the following properties:

melting temperature: about 260° C.;
 stress at break at 200° C.: about 4 MPa;
 yield stress at 200° C.: about 3 MPa.

The methods for determining these properties will be described hereinafter.

Generally, superior mechanical properties are obtained with TFE/perfluoroalkylvinylether copolymers, in particular with perfluoropropylvinylether, as described in U.S. Pat. No. 3,635,926, independently from the melt viscosity.

The performances of this class of copolymers improve as the number of carbon atoms of the perfluoroalkylvinylether alkyl group increases, even though the reactivity decreases when the perfluoroalkyl segment length increases, still remaining, however, more reactive than the corresponding alpha-alkyl-perfluoroolefins. The low reactivity of Perfluoropropylvinylether leads to a decrease in the productivity of the polymerization reactor, with negative consequences on the production costs, and requires recovery of the unreacted monomer when the reaction is over (see for instance British Patent 1,514,700). Also this drawback makes the process for producing TFE copolymers with perfluoropropylvinylether and other perfluorovinylethers with even longer perfluoroalkyl chain more expensive.

Therefore, the need of finding new combinations of fluorinated monomers is particularly felt, which, on one hand, could be a clear improvement with respect to FEP copolymers and terpolymers and, on the other hand, preserve a set of properties comparable to those, for instance, of the copolymers of tetrafluoroethylene with perfluoropropylvinylether, remedying at the same time the shortcomings described above.

It has now been surprisingly found that TFE thermoprocessable copolymers with definite amounts of perfluoromethylvinylether and one or more fluorinated dioxoles as described hereinbelow, are unexpectedly endowed with a very good combination of thermal and mechanical properties at high temperatures (even at 250° C.) and of stress resistance, making them particularly suitable for coating electric cables by melt extrusion. The superior properties of these copolymers are particularly unexpected since the performances of the thermoprocessable copolymers of tetrafluoroethylene (TFE) with perfluoromethylvinylether alone are clearly inferior to those of the TFE-perfluoropropylvinylether copolymers. A particular advantage of these copolymers, object of the present invention, derives from the fact that perfluoromethylvinylether results, in the copolymerization with TFE, by far more reactive than both perfluoroalkylvinylethers with a perfluoroalkyl chain having a higher number of carbon atoms and hexafluoropropene.

It has also been found, according to the present invention, a new class of perfluorodioxoles suitable for preparing homopolymers and copolymers provided with superior mechanical properties and a good thermal stability. These new perfluorodioxoles are particularly suitable for preparing said thermoprocessable tetrafluoroethylene copolymers.

Different classes of fluorodioxoles are known. U.S. Pat. No. 3,865,845 describes, in particular, the following compound:

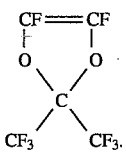

European patent application 76,581 describes the following class of compounds:

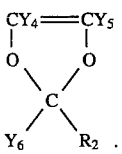

where $Y_4$, $Y_5$ and $Y_6$ are F or Cl while $R_2$ is a perfluoroalkyl radical having from 1 to 4 carbon atoms.

European patent application No. 80,187 describes 2,2,4,5-tetrafluoro-1,3-dioxole

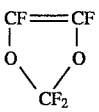

which in the following will be indicated with PD.

From these fluorodioxoles, homopolymers and copolymers, in particular with tetrafluoroethylene, and terpolymers, in particular with tetrafluoroethylene and another monomer with olefinic unsaturation, can be obtained. These homopolymers, copolymers and terpolymers are described in particular in the following patents or patent applications: U.S. Pat. No. 3,865,845, U.S. Pat. No. 3,978,030, EP-73,087, EP-76,581 and EP-80,187.

A drawback of the known fluorodioxoles is that they have a strong tendency to homopolymerizing spontaneously. This causes problems during storage and, in certain cases, in preparing copolymers with other monomers with a homogeneous monomer distribution along the polymeric chain. This problem especially arises in the preparation of amorphous copolymers (namely, copolymers containing more than about 10–12% by moles of fluorodioxole).

The preparation of PD is preferably carried out in tetrahydrofuran, as described in U.S. Pat. No. 4,558,141. In spite of the difference in the boiling points of PD and tetrahydrofuran (67° C.), about 1% of tetrahydrofuran is always present in perfluorodioxole after distillation. As a rule, tetrahydrofuran in PD must be eliminated before proceeding to PD polymerization, for instance by treatment with water and subsequent distillation. This further steps, which render the process even more cumbersome, are necessary because even small amounts of tetrahydrofuran cause variations in the final polymer characteristics, by substantially reducing the molecular weight of the polymer as such. For instance, the glass transition temperature ($T_g$) of the homopolymer varies from 172° to 84°–92° C. when the tetrahydrofuran content in the dioxole ranges from 0% to 2%. The perfluorodioxole, purified from tetrahydrofuran to avoid homopolymerization, must be kept at −78° C. or in 1,1,2-trichloro-1,2,2-trifluoroethane solutions, however cooled.

It has now been found a new class of perfluorodioxoles which, surprisingly, do not tend to homopolymerize spontaneously, thus they can be kept at room temperature after a conventional distillation.

It has also been found that these new fluorinated dioxoles confer to the above indicated thermoprocessable copolymers mechanical properties superior to those obtainable with the fluorodioxoles of the prior art.

It is known that fluorodioxoles are obtained from the corresponding dioxolanes containing two Cl atoms, one in position 4 and the other in position 5, by dehalogenation with a metal, in particular Mg: said reaction is carried out in a solvent, in particular dimethylformamide (in this respect, see the above mentioned patents and patent applications U.S. Pat. No. 3,865,845, EP-76,581 and EP-80,187).

Such dehalogenation constitutes a problem in the perfluorodioxole synthesis, because it usually gives low yields. According to International patent application WO 91/03472, the dehalogenation yield increases if, in the starting dioxolane, the relative amount of anti isomer (in which the two chlorine atoms are in anti position) is higher than that of sin isomer (in which the two chlorine atoms are in sin position). A certain increase in the relative amount of anti isomer is obtained by treating the mixture of isomers with $SbCl_5$ and HF.

There have now been found three processes for preparing the new perfluorodioxoles object of the present invention, through the corresponding dioxolanes containing two Cl atoms. Such processes grant a very good yield in the dehalogenation reaction without enriching the starting dioxolanes in anti isomer.

Therefore, an object of the present invention is to provide a new class of perfluorodioxoles which do not homopolymerize spontaneously, hence their storage does not cause problems and their use in copolymerization reactions does not cause problems of dishomogeneity in the monomer distribution along the polymer chain.

Another object of the present invention is to provide processes for the preparation of the above perfluorodioxoles, in which the final dehalogenation occurs with high yields.

A further object is to provide new homopolymers and copolymers of the above mentioned perfluorodioxoles endowed with good mechanical properties and good thermal stability.

A further object of the present invention is to provide new thermoprocessable copolymers of tetrafluoroethylene which overcome the drawbacks encountered when preparing and using the thermoprocessable tetrafluoroethylene copolymers of the prior art.

A further object is to provide new thermoprocessable tetrafluoroethylene copolymers, suitable, in particular, for coating electric cables by melt extrusion.

In the description of the present invention, the word "copolymer" is used to designate—depending on the circumstances—copolymerization products of 2, 3, 4 or more monomers.

One of the above mentioned objects is achieved with the new thermoprocessable tetrafluoroethylene copolymers of the present invention.

These copolymers are constituted by:

a) from 0.5 to 13% by weight of perfluoromethylvinylether;

b) from 0.05 to 3% by weight of one or more fluorinated dioxoles of formula:

(XIII)

wherein: $Z^1$ and $Z^2$, equal or different from each other, are F, Cl, H or $OR^1T$ where $R^1$ is a perfluoroalkylene radical having from 1 to 5 carbon atoms, and T is F or Cl, with the proviso that $Z^1$ and $Z^2$ cannot be both Cl or $OR^1T$; $Y^1$ and $Y^2$, equal or different from each other, are F or $CF_3$;

c) tetrafluoroethylene, in such an amount that the sum of the percentages of the various monomers is equal to 100% by weight.

The preferred percentages by weight of the three types of monomers is the following:

perfluoromethylvinylether: 2–9%;
total fluorodioxole or fluorodioxoles: 0.1–1.5%;
tetrafluoroethylene: difference to 100%.

The copolymers according to the present invention contain preferably only one fluorodioxole.

Among the preferred fluorodioxoles, 4,5-difluoro-2,2-trifluoromethyl-1,3-dioxole, perfluorodioxole PD and the new perfluorinated dioxoles, which are described hereinbelow, can be cited.

The thermoprocessable copolymers object of the present invention can be prepared by radical polymerization both in aqueous and in organic medium. The polymerization in aqueous medium can be carried out as follows. The polymerization initiator can be any substance capable of producing radicals such as, for instance, a peroxide, a persulphate or an azocompound. These compounds generally have, in the reaction conditions, an average lifetime sufficient to maintain the reaction and to obtain the desired molecular weight. Optionally a reducing agent can be added, acting as promoter for the initiator decomposition, such as an iron salt. The employed amount of initiator depends, as known, on the reaction temperature, on the possible presence of chain transfer agents, on the desired molecular weight and, generally, on the reaction conditions. Moreover, the polymerization in aqueous medium requires the presence of a surfactant. It is possible to use the salts of perfluoroalkyl carboxylic acids (for instance ammonium perfluorocaprilate). Other suitable compounds are perfluoroalkoxybenzenesulphonic acid salts, described for instance in European patent application No.184,459. Optionally, it is possible to add to the aqueous medium substances which are solvents for the monomers and optionally for the initiator. These solvents can be, for instance, 1,1,2-trichloro-1,2,2-trifluoroethane, 1,2-dichloro-1,1,2,2-tetrafluoroethane, trichlorofluoromethane, dichlorodifluoromethane, $CClF_2H$, and perfluorocyclobutane.

It results particularly advantageous to carry out the polymerization in aqueous phase in the presence of perfluoropolyethers. They can be added to the reaction medium in the form of aqueous emulsion in the presence of a suitable dispersing agent, as described in European patent No. 247, 379, or, preferably, in the form of a thermodynamically stable aqueous microemulsion, as described in U.S. Pat. No. 4,864,006.

Alternatively, polymerization can be carried out in a liquid organic medium, as described, for instance, in U.S. Pat. No. 3,642,742. Any suitable initiator for the polymerization of TFE in organic medium can be used. Preferably, the initiator must be soluble in the reaction solvent. Examples of suitable initiators are alkyl percarbonates and perfluoroacylperoxides.

The comonomers are usually fed into the reactor in the form of gaseous mixture.

The new perfluorodioxoles constituting a further object of the present invention, have the formula:

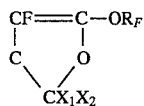
(I)

wherein $R_F$ is a perfluoroalkyl radical having from 1 to 5 carbon atoms, and $X_1$ and $X_2$, equal or different from each other, are F or $CF_3$.

Preferably, $X_1$ and $X_2$ are both fluorine atoms.

Among the preferred perfluorodioxoles, the following can be cited:

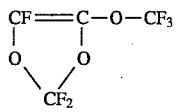
(IV)

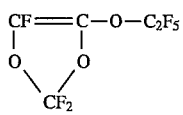
(V)

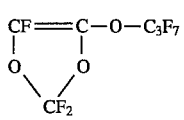
(VI)

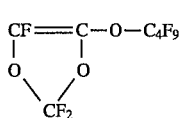
(VII)

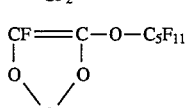
(VIII)

The most preferred perfluorodioxoles are those of formula (IV) or (V).

The perfluorodioxoles of formula (I) can be prepared by the following process (called hereinafter "first process"), which comprises:

1°) reacting at a temperature of from −140° C. to +60° C. (and preferably from −110° C. to −20° C.) a dioxole of formula:

(II)

(wherein $X_1$ and $X_2$, equal or different from each other, are F or $CF_3$) with a fluorooxycompound of formula $R_F OF$ (wherein $R_F$ is a perfluoroalkyl radical having from 1 to 5 carbon atoms), obtaining a dioxolane of formula:

(III)

2°) dehalogenating the dioxolane (III) by reaction with a metal in an aprotic dipolar solvent, according to known techniques.

The dioxoles of formula (II) are known compounds; they can be prepared for instance according to the process described in European patent application No. 460,946.

The fluorooxycompounds of formula $R_F$—OF are also known compounds. $CF_3OF$ can be prepared, for instance, by the process described by G. H. Cady and K. B. Kellogg, J. Am. Chem. Soc. 70, 3986, 1948; the superior homologues by the process described in U.S. Pat. No. 4,827,024.

In the first step, the dioxole (II) is present in liquid phase. Preferably, it is dissolved in a solvent. Suitable solvents are chlorofluorocarbons and perfluoropolyethers having perfluoroalkyl end groups, in particular those having an average numeric molecular weight between 500 and 1,000. Among chlorofluorocarbons, $CFCl_3$, $CF_2Cl_2$ and $CFCl_2$—$CF_2Cl$ can be cited. Among perfluoropolyethers, commercial products Galden® and Fomblin® by Ausimont, Krytox® by Du Pont de Nemours, and Demnum® by Daikin can be cited; an example of suitable perfluoropolyether is Galden® DO2 of formula:

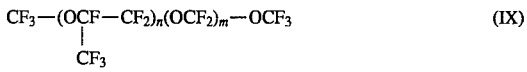
(IX)

having n/m equal to 40 and an average number molecular weight of 760.

The fluorooxy compound $R_F$—OF can be fed all at the same time in the above mentioned liquid phase. However, it is more worthwhile, from an industrial point of view, to feed it continuously, usually in the gas state, in the liquid phase. Preferably, the gaseous fluorooxy compound is fed with a diluent gas, inert in the reaction conditions, in particular $N_2$, He or Ar. When a diluent gas is used, the volume ratio between such a gas and $R_F$—OF is generally from 3 to 10 and, more commonly, from 3 to 6.

The subsequent dehalogenation can be carried out with one of the known methods. The process described in European patent application No. 499,158 of the Applicant itself is particularly suitable, according to which the dioxolane, dissolved in a dipolar aprotic solvent, is reacted with zinc at a temperature of from 30° to 130° C. Particularly suitable solvents are dimethylsulphoxide, dimethylformamide, and glymes.

The new perfluorodioxoles object of the present invention can be prepared with another process (called hereinafter "second process"), which comprises:

1°) reacting at a temperature of from −140° C. to +60° C. (and preferably from −110° C. to −20° C.) an olefin of formula $$R_F-O-CCl=CFCl \quad (X)$$

(wherein $R_F$ is a perfluoroalkyl group having from 1 to 5 carbon atoms) with a bisfluorooxy compound of formula $$CX_1X_2(OF)_2 \quad (XI)$$

(wherein $X_1$ and $X_2$, equal or different from each other, are F or $CF_3$), obtaining a dioxolane of formula:

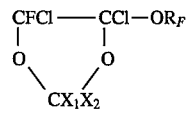
(III)

2°) dehalogenating the dioxolane (III) by reaction with a metal in an aprotic dipolar solvent.

Olefin (X) can be prepared by reacting $CCl_{2=CCl2}$ with $R_FOF$, to obtain $R_F-OCCl_2-CFCl_2$ which, by dechlorination reaction with zinc powder in an organic solvent, yields olefin (X).

It has been surprisingly found that, contrary to the teaching of the prior art, it is not necessary to start from a mixture of isomers of dioxolane (III) (obtained either with the first or with the second process) enriched in anti isomer to achieve a high yield in the final dehalogenation: in fact, high yields are unexpectedly obtained either when the sin or the anti isomer prevails in the dioxolane.

The new perfluorodioxoles object of the present invention can also be prepared with a further process (called hereinafter "third process"), which comprises reacting a gaseous flow of a dioxolane of formula

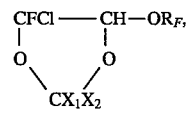
(XI)

optionally in mixture with a dioxolane of formula

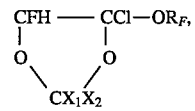
(XII)

with KOH in the solid state, at a temperature of from 20° to 150° C. This reaction causes dehydrochlorination with formation of dioxole (I). The reaction occurs with high yields.

The starting dioxolane (XI) can be obtained as follows: $R_FOF$ is reacted with trichloroethylene, obtaining $R_FO-CClH-CFCl_2$ which is dechlorinated with zinc powder in an organic solvent, obtaining the olefin $R_F-OCH=CFCl$. By reacting the olefin with $CX_1X_2(OF)_2$, dioxane (XI) is obtained.

Dioxolane (XII), in admixture with dioxolane (XI), can be obtained as follows: $CClH=CClH$ is reacted with $CX_1X_2(OF)_2$, obtaining the dioxolane

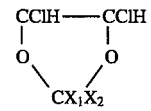

which by dehydrohalogenation with solid KOH gives the dioxole

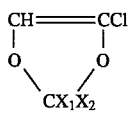

The dioxole is reacted with $R_FOF$, obtaining a mixture of dioxolanes (XI) and (XII).

The synthesis of the new perfluorodioxoles can be made, analogously to the methods described above, by using 1,2-dichloroethylene, 1,1-dichloroethylene or trichloroethylene, and hypofluorites of formulas $$R_F-OF \text{ and } (CX_1X_2)OF_2,$$

alternating dechlorination and dehydrochlorination reactions for the synthesis of the reaction intermediates.

After distillation, the perfluorodioxoles (I), object of the present invention, can be stored at room temperature without any spontaneous polymerization.

A further object of the present invention are the homopolymers of the new fluorodioxoles (I) and their copolymers with one or more comonomers having olefinic unsaturation. Among them, the preferred comonomers are: tetrafluoroethylene, vinylidene fluoride, vinyl fluoride, trifluoroethylene, perfluoropropene, perfluoromethylvinylether, perfluoroethylvinylether, perfluoropropylvinylether, perfluorodioxole PD, perfluoro(2,2-dimethyl)-1,3-dioxole, $CF_2=CF-O-CF_2-CF_2-SO_2F$, chlorotrifluoroethylene, vinyl chloride, methyl acrylate, methyl methacrylate, and ethylene.

Preferred copolymers are those with tetrafluoroethylene, in particular those of $C_2F_4$ and 2,2,4-trifluoro-5-trifluoromethoxy- 1,3-dioxole (IV).

The polymerization (for the preparation both of homopolymers and of copolymers) can be carried out in a solvent or in aqueous emulsion. The solvent is generally selected from chlorofluorocarbons and perfluoropolyethers, as cited above. The reaction is carried out by means of the radicalic initiators commonly used for the polymerization of TFE, for instance perfluoropropionylperoxide, benzoylperoxide, azobis(isobutyronitrile), and percarbonates. Moreover, redox systems, such as for instance those described in Prog. Polym. Sci., Vol. 8, p. 61, 1982, can be used.

For instance, generally employable polymerization methods in an aqueous medium are described in European patent application No. 247,379 and in US Patent No. 4,846,006; generally employable polymerization methods in a non-aqueous medium are described in U.S. Pat. Nos. 4,864,006 and 5,182,342.

By homopolymerizing, for instance, 2,2,4-trifluoro-5-trifluoromethoxy- 1,3-dioxole (IV), homopolymers are obtained of formula:

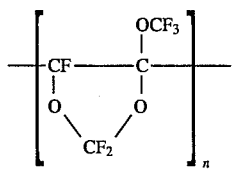
(IX)

The homopolymers with n=4–7 are viscous oils; with n>10, transparent solids are obtained.

The oils obtained by homopolymerization of the perfluorodioxoles object of the present invention are useful in particular as lubricating oils and oily components for lubricating greases; the solid polymers are particularly suitable for coatings having low diffraction index, in particular for optical fibers.

The copolymers of the perfluorodioxoles object of the present invention with tetrafluoroethylene are crystalline if the content in fluorodioxole is relatively low, and amorphous if the content is relatively high. It is not easy to establish a clear boundary between the two types of polymers: crystalline products are generally obtained with a perfluorodioxole content lower than about 10–12% by moles, amorphous products with a perfluorodioxole content higher than about 10–12% by moles.

The crystalline copolymers are useful, additionally, as dielectric materials. The amorphous copolymers are useful, additionally, as coating for articles to be electrically insulated. Moreover, due to their low refraction index, they are suitable for optical fiber coatings.

The copolymers and terpolymers according to the present invention can contain an amount of perfluorodioxoles from about 0.1% to 70% by moles and more, i.e. up to polymers containing only a few percent of monomer or monomers different from perfluorodioxole.

The following examples are given for illustrative purpose and they cannot be construed as limitative of the scope of the present invention.

EXAMPLE 1

Preparation of 4,5-dichloro-2,2,4-trifluoro-5-trifluoro-methoxy-1,3-dioxolane (1st process)

In a 250 ml multi-necked cylindrical glass reactor equipped with: mechanical stirrer, thermocouple, dipping inlet for the reaction gaseous mixture, outlet with inert gas flow, 63 g of 4,5-dichloro-2,2-difluoro-1,3-dioxole (356m moles) and 200 ml of $CF_2Cl_2$ as solvent were loaded. The reactor was then brought by means of a cryostat to $-100°$ C.; at this point, under mechanical stirring, a mixture of $CF_3OF$ (1.3 nl/h) and helium (6 nl/h) was continuously fed for 7.0 hours. Then, in helium flow (1 nl/h), the temperature was raised to $-70°$ C. to eliminate the excess of $CF_3OF$. From the reaction product, after distillation of the most part of the solvent, the reaction products were separated by fractional distillation on a plate column at atmospheric pressure. The fraction having boiling point 77°–78° C., constituted by 73.0 g of 4,5-dichloro- 2,2,4-trifluoro-5-trifluoromethoxy-1,3-dioxolane, was collected. The so isolated dioxolane consisted of a blend of two isomers, anti isomer (91%) where the two Cl atoms are in anti position, and isomer sin (9%) where the two Cl atoms are in sin position. In the fraction having boiling point 47°–50° C., 10.2 g of 4,5-dichloro-2,2,4,5-tetrafluoro-1,3-dioxolane with an isomeric sin/anti ratio of 68/32 were isolated. The conversion of the starting dioxole was complete. The yield in 4,5-dichloro-2,2,4-trifluoro-5-trifluoro-methoxy-1,3-dioxolane, defined as ratio between the obtained dioxolane moles and the starting dioxole moles, was 73%.

Characterization of 4,5-dichloro-2,2-4-trifluoro-5-trifluoro-methoxy-1,3-dioxolane.

Boiling point at atmospheric pressure: 77.5° C.
$^{19}F$ NMR spectrum in p.p.m. from $CFCl_3$=0.
Anti isomer:
(2F O—CF'F"—O) F'=–55.2; F"=–58.6 JF'F"=67Hz;
(3F—$OCF_3$) –55.0; (1F—CFCl—) –67.3.
Sin isomer:
(2F O—CF'F"—O) F'=–55.7; F"=–57.2 JF'F"=66Hz;
(3F—$OCF_3$) –54.8; (1F—CFCl—) –60.6.

Mass spectrum (electronic impact), main peaks and relevant assignments:
245 (M+–Cl), 179 ($C_3F_4O_2Cl+$), 132 ($C_2F_4O_2+$), 85 ($CF_2Cl+$),
69 ($CF_3$ 100%)
Infrared spectrum, main bands (cm$^{-1}$):
1282, 1206 1094, 1043, 940 898, 877, 843.

EXAMPLE 2

Dehalogenation of 4,5-dichloro-2,2,4-trifluoro-5-trifluoro-methoxy-1,3-dioxolane (1st process).

In a 1 l three-necked flask, equipped with magnetic stirrer, thermometer, condenser and connected to a trap maintained at $-75°$ C., 33.8 g of zinc powder, activated by washing with HCl 3N, 600 ml of DMF and 100 mg of I2 were charged under nitrogen atmosphere. The internal temperature was brought to 90° C. and 47.2 g of 4,5-dichloro-2,2,4-tri-fluoro-5-trifluoromethoxy-1,3-dioxolane (168 mmoles), prepared as in Example 1, were added dropwise. During the addition, the temperature increased up to 98° C. When the addition was over, the reaction mixture was stirred for 1 additional hour at 90° C. In the cold trap 26.1 g (124 mmoles) of 2,2,4-trifluoro- 5-trifluoromethoxy-1,3-dioxole condensed. The dioxole yield, defined as ratio between the obtained dioxole moles and the starting dioxolane moles, was 74%.

Characterization of 2,2,4-trifluoro-5-trifluoromethoxy-1,3-dioxole:

Boiling point at atmoshperic pressure: 24° C.
$^{19}F$ NMR spectrum in p.p.m. from $CFCl_3$=O
–147.1 (1F, =CF—), –61.3 (3F, $CF_3$—), –47.0 (2F, —$OCF_2O$).

Mass spectrum (electronic impact), main peaks and relevant assignments:
210 (M+), 191 (M+–F), 135 ($C_2F_5O$), 69 ($CF_3$ 100%)
Infrared spectrum, main bands (cm$^{-1}$): 1850, 1394, 1276, 1239, 1189, 1068, 997.

EXAMPLE 3

Dehalogenation of 1,2,2-tetrachloro-1-fluoro-2-trifluoro-methoxyethane (2nd process).

In a 1 l three necked flask, equipped with magnetic stirrer, thermometer, dropping funnel, and connected through a Vigreux column and a condenser to a trap maintained at $-75°$ C., 80.0 g of zinc powder, activated by washing with HCl 3N, 550 ml of DMF and 50 mg of KI were charged under nitrogen atmosphere. The internal temperature was brought to 80° C. and 102.0 g of 1,1,2,2-tetrachloro-1-fluoro-2-trifluoromethoxyethane (377mmoles), were added dropwise. During the addition, the temperature increased up to 90° C. When the addition was over, the reaction mixture was stirred for 1 additional hour at 90° C. In the cold trap 62.8 g (315 mmoles) of 1,2-dichloro- 1-fluoro-2-trifluoromethoxyethane (cis/trans 50%/50%) condensed. The 1,2-dichloro-1-fluoro-2-trifluoromethoxyethene (trans+cis) yield was 83%.

EXAMPLE 4

Preparation of 4,5-dichloro-2,2,4-trifluoro-5-trifluoro-methoxy- 1,3-dioxolane (2nd process).

In a 150 ml multi-necked cylindrical glass reactor equipped with: mechanical stirrer, thermocouple, dipping inlet for the reaction gaseous mixture, outlet with inert gas flow, 11.5 g of 1,2-dichloro-1-fluoro-2-trifluoromethoxy-ethene (57 mmoles) and 50 ml of $CF_2Cl_2$ as solvent were introduced. The reactor was then brought by means of a cryostat to −50° C.; then, under mechanical stirring, a mixture of $CF_2(OF)_2$ (0.4 nl/h) $CO_2$ (0.2 nl/h) and helium (3 nl/h) was continuously fed for 1.7 hours; at the end of the addition the reaction was complete. Then, under a helium flow (1 nl/h), the excess of $CF_2(OF)_2$ was eliminated.

From the reaction mixture, after stripping the most part of the solvent, the reaction products were separated by fractional distillation on a plate column at atmospheric pressure. The fraction having boiling point 77°–80° C. constituted by 5.6 g of 4,5-dichloro-2,2,4-trifluoro-5-trifluoromethoxy-1,3-dioxolane was collected. The so isolated dioxolane was formed by a mixture of two isomers, anti isomer (33%), where the two Cl atoms are in anti position, and sin isomer (67%) where the two Cl atoms are in sin position. The starting olefin conversion was complete. The 4,5-dichloro-2,2,4-trifluoro-5-trifluoromethoxy-1,3-dioxolane yield, defined as ratio between the obtained dioxolane moles and the starting $CF_2(OF)_2$ moles, was 66%.

EXAMPLE 5

Dehalogenation of 4,5-dichloro-2,2,4-trifluoro-5-trifluoro-methoxy- 1,3-dioxolane (2nd process).

In a 100 ml three necked flask, equipped with magnetic stirrer, thermometer, condenser, and connected to a trap maintained at −75° C., 2.0 g of zinc powder, activated by washing with HCl 3N, 12 ml of DMF and 10 mg of $I_x$ were charged under nitrogen atmosphere. The internal temperature was brought to 90° C. and 1.66 g of 4,5-dichloro-2,2,4-trifluoro-5-trifluoromethoxy- 1,3-dioxolane, prepared as in Example 4, were added dropwise. During the addition, the temperature increased up to 94° C. When the addition was over, the reaction mixture was stirred for 30 additional minutes at 90° C. In the cold trap 0.950 g of a mixture containing 80% of 2,2,4-trifluoro-5-trifluoromethoxy- 1,3-dioxole, and 20% of the starting product, having the same sin/anti ratio of the starting dioxolane, condensed. The dioxole yield on the converted product, defined as ratio between the obtained dioxole moles and the reacted dioxolane moles, was 69%.

EXAMPLE 5 bis

Dehalogenation of 4,5-dichloro-2,2,4-trifluoro-5-trifluoro-methoxy- 1,3-dioxolane (2nd process).

In a 250 ml three necked flask, equipped with magnetic stirrer, thermometer, condenser, and connected to a trap maintained at −75° C., 11.6 g of zinc powder, activated by washing with HCl 3N, 105 ml of DMF and 20 mg of $I_2$ were charged under nitrogen atmosphere. The internal temperature was brought to 45° C. and 40 g of 4,5-dichloro-2,2,4-trifluoro- 5-trifluoromethoxy-1,3-dioxolane, prepared as in Example 4, were added dropwise. During the addition, the temperature increased up to 53° C. When the addition was over, the reaction mixture was stirred for 1 additional hour at 45° C. In the cold trap 24.0 g of 2,2,4-trifluoro-5-trifluoromethoxy-1,3-dioxole condensed, containing traces of the starting product. The reactor was brought to 20° C. and the pressure reduced to 300 mmHg. After 30 minutes, 3.5 g of a mixture containing 90% of the desired product, 3% of the starting product, and 7% of dimethylformamide, were collected. The dioxole yield on the converted product, defined as ratio between the obtained dioxole moles and the reacted dioxolane moles, was 91%.

EXAMPLE 6

Dehydrochlorination of 4-chloro-2,2,4-trifluoro-5-trifluoro-methoxy-1,3 -dioxolane (3rd process).

In a tubular steel reactor, having a 3 cm diameter and a 50 cm length, provided with inlet and outlet of the reacting gases, 170 g of KOH pellets were charged, previously mixed with 170 g of glass rings as filling; the so loaded reactor was evacuated ($10^{-3}$ mmHg) and heated to 102° C. The inlet of the reacting gases was connected to a flask containing 3.7 mmoles of 4-chloro-2,2,4-trifluoro-5-trifluoromethoxy-1,3-dioxolane kept at −45° C., the reactor outlet was connected to a collecting trap kept at −196° C. The starting product vapours from the trap at −45° C. passed through KOH kept at 102° C., where they reacted, and were collected into the trap at −196° C. 3.4 mmoles of a mixture containing 2.4 mmoles of 2,2,4-trifluoro- 5-trifluoromethoxy-1,3-dioxole and 0.9 mmoles of the starting product were collected in the trap at −196° C. The 4-chloro- 2,2-4-trifluoro-5-trifluoromethoxy-1,3-dioxolane conversion was 75%; the dioxole yield on the converted product was 85%.

EXAMPLE 7

Thermoprocessable tetrafluoroethylene copolymer

A 5 l AISI 316 chromium plated steel autoclave was employed, equipped with a stirrer working at 650 rpm. After evacuation, 3 l of demineralized water, $CHCl_3$ as chain transfer agent in an amount of 0.67 ml/$l_{H2O}$, and the dioxole of formula (IV) in an amount of 2.1 g/$l_{H2O}$ (equivalent to 0.01 mole/$l_{H2O}$), and eventually an aqueous microemulsion of perfluoropolyether prepared according to Example 1 of U.S. Pat. No. 4,864,006, so as to have 2 g of surfactant/$l_{H2O}$, were charged. The autoclave was heated to 75° C. A TFE/perfluoromethylvinylether (FMVE) gaseous mixture in molar ratio 37.5/1 was added by means of a compressor until a pressure of 20 absolute bar was reached. The gaseous mixture composition in the autoclave was analyzed by gaschromatography.

Before the reaction start, the gaseous phase had the following composition (% by moles): 80.9% TFE, 15.8% FMVE, 3.2% dioxole. Then, by means of a dosing pump, a 0.0215 molar solution of potassium persulphate with a flow rate of 88 ml/hour, was fed continuously.

The polymerization pressure was kept constant by feeding the above said monomeric mixture, and when 780 g had been fed, the reaction was stopped. The composition of the final gaseous phase was the following (% by moles): 87.73% TFE, 12% FMVE; 0.27% dioxole. The reactor was cooled to room temperature; the emulsion was discharged and coagulated by addition of $HNO_3$ (65%). The polymer was separated, washed with water and dried. Table 1 reports the data relating to the polymer characterization. The characteristics and performances of the terpolymer were determined as follows. The melt viscosity was measured according to ASTM D-1238-52T standard, using a modified device in which the cylinder, the nozzle and the piston were made of corrosion resistant steel. 5 g of the sample were introduced into the cylinder having a 9.53 mm internal diameter, kept at 372±1° C. After 5 minutes, the molten polymer was extruded through a capillary tube having a 2.10 mm diameter and a 8.0 mm length with a 5 kg load (piston+additional weight), corresponding to a shear stress of 0.457 kg/cm$^2$.

The melt viscosity in poise was calculated on the basis of the equipment geometry and was obtained dividing 53150 by the observed extrusion rate, expressed in grams/minute.

The terpolymer composition was determined by mass balance.

The melting temperature was determined by Differential Scanning Calorimetry (DSC) using a Perkin-Elmer Mod. IV calorimeter. About 10 mg of the sample to be analyzed were heated from room temperature to 350° C. with a 10° C./min rate. The sample was maintained at 350° C. for 5 min. and then cooled to room temperature with a 10° C./min rate. The heating process at 350° C. was repeated with the same modalities. During this step, the temperature corresponding to the maximum of the melting endotherm curve was registered and indicated as "second melting temperature" [$T_m(II)$].

For the determination of tensile properties (tensile stress and elongation at break, yield stress, yield elongation and Young modulus), some plaques having a 1.58±0.08 mm thickness were prepared by compression molding, according to ASTM D-3307-81 standard. Micro-specimens were obtained therefrom to measure mechanical properties according to ASTM D-1708 standard. In all these measurements, the stretching rate was 50 mm/min. Usually, for each polymer sample, 3 measurements were carried out, at room temperature, at 200° C., and at 250° C. When working at high temperatures, the specimen was kept at the test temperature for 5 min before the measurement.

To determine the stress resistance, the standard equipment described in ASTM D-2176-63T for the MIT Flex Life was used. The measurement was carried out on specimens obtained from a 0.3 mm thick film. The specimen was gripped in the jaws of the equipment and a 1 kg weight was applied thereto. The film was bent to a 135° angle rightward with respect to the vertical line and with the same angle leftward, with a rate of 175 cycles per minute. The number of cycles necessary to achieve the breakage of the specimen was registered. On each sample six measurements were carried out, and the average value was reported.

EXAMPLE 8

Thermoprocessable tetrafluoroethylene copolymer.

The perfluorodioxole PD described in European patent application No. 80,187, having formula

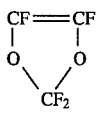

was used.

It was operated as in Example 7, with the difference that 1.43 g/l$_{H2O}$ (equivalent to 0.01 mole/l$_{H2O}$) of perfluorodioxole PD were fed. The starting gaseous phase had the following composition (% by moles): TFE 84.8, FMVE 12.2, and PD 3.0; while the final composition was: TFE 88, FMVE 12, PD 0. Table 1 reports the data relating to polymer characterization.

Upon examining Table 1, we can notice that the thermoprocessable copolymers according to the present invention have melting temperature and mechanical properties clearly better than those of FEP terpolymers.

Moreover, upon comparing the data of Example 7 (relating to a new perfluorodioxole according to the present invention) with those of Example 8 (relating to a known perfluorodioxole), we can notice that the former unexpectedly confers to said copolymer a superior "flex life" and improved mechanical properties at high temperatures, especially at 250° C., as regards breaking stress and elongation at break.

TABLE 1

| COMPOSITION, PROPERTIES | EXAMPLE 7 | EXAMPLE 8 |
|---|---|---|
| FMVE | | |
| % by moles | 2.6 | 2.6 |
| % by weight | 4.3 | 4.3 |
| Dioxole | | |
| % by moles | 0.3 | 0.3 |
| % by weight | 0.77 | 0.53 |
| Melt Flow Index (g/10') | 9 | 9 |
| $T_m$ (II) (°C.) | 294.4 | 297 |
| Flex life | 2332 | 843 |
| Properties at 23° C. | | |
| Elastic Modulus (MPa) | 487 | 488 |
| Yield Stress (MPa) | 13.6 | 13.6 |
| Stress at Break (MPa) | 24 | 20.5 |
| Elongation at Break (%) | 333 | 297 |
| Properties at 200° C. | | |
| Elastic Modulus (MPa) | 45 | 50 |
| Yield Stress (MPa) | 2.9 | 3.0 |
| Stress at Break (MPa) | 6.9 | 6.3 |
| Elongation at Break (%) | 291 | 264 |
| Properties at 250° C. | | |
| Elastic Modulus (MPa) | 25 | 30 |
| Yield Stress (MPa) | 1.9 | 2.0 |
| Stress at Break (MPa) | 4.4 | 3.2 |
| Elongation at Break (%) | 364 | 158 |

EXAMPLE 9

Crystalline copolymer between $C_2F_4$ and TTD (2,2, 4-trifluoro-5-trifluoromethoxy- 1,3-dioxole)

Into a 42 ml glass polymerization reactor, equipped with magnetic stirrer and inlet for feeding and discharging the reagents, 8 ml of $CCl_2FCF_2Cl$, 1.5 ml of a 0.35% solution of perfluoropropionylperoxide in $CCl_2FCF_2Cl$, 0.33 mmoles of 2,2,4-trifluoro- 5-trifluoromethoxy-1,3-dioxole and 10 mmoles of tetrafluoroethylene were introduced. The reactor was then brought to −196° C. and evacuated. After letting it warm up to room temperature, the reactor was heated to and kept at 40° C. for 8 hours under stirring. The raw reaction product appeared as a gelatinous mass. The reactor was brought to the temperature of liquid nitrogen, connected to a vacuum pump and maintained at a pressure of 10$^{-3}$ mbar; then it was let warm up to room temperature, subdividing the evolved vapours by means of cool traps at −90° C., −120° C. and −196° C. The trap at −90° C. contained only $CFCl_2CF_2Cl$. The trap at −120° C. contained 0.70 mmoles of $CFCl_2CF_2Cl$ and 0.23 mmoles of unreacted dioxole. The trap at −196° C. contained 1.10 moles of unreacted $C_2F_4$. After distillation of the solvent and of the unreacted monomers and stripping of the polymer under vacuum at 120° C. for 2 hours, 0.910 g of polymer were isolated. The weight balance determined by g.l.c. of the traps containing the unreacted monomers allowed to calculate the molar percentage of dioxole in the polymer which resulted to be 1.1%.

The melting point was determined by DSC: the polymer melted at 305.0° C. with a melting ΔH of 9.8 cal/g; the Thermal Gravimetric Analysis (TGA) showed a weight loss of 2% at 448° C. and of 10% at 530° C. The polymer was compression moulded (at 330° C., 122 arm) into a transparent and strong film.

EXAMPLE 10

Crystalline copolymer between $C_2F_4$ and TTD

In a 42 ml glass polymerization reactor, equipped with magnetic stirrer and inlet for feeding and discharging the reagents, 15 ml of $CCl_2FCF_2Cl$, 3.0 ml of a 0.35% solution of perfluoropropionylperoxide in $CCl_2FCF_2Cl$, 1.17 mmoles of 2,2,4-trifluoro- 5-trifluoromethoxy-1,3-dioxole and 20 mmoles of tetrafluoroethylene were introduced. The reactor was then brought to −196° C. and evacuated. After letting it warm up to room temperature, the reactor was heated to and kept at 40° C. for 8 hours under stirring. The raw reaction product appeared as a gelatinous mass. The reactor was brought to the temperature of liquid nitrogen, connected to a vacuum pump and maintained at a pressure of $10^{-3}$ mbar; then it was let warm up to room temperature, subdividing the evolved vapours by means of cool traps at −85° C., −120° C. and −196° C. The trap at −85° C. contained only $CFCl_2CF_2Cl$. The trap at −120° C. contained 2.90 mmoles of $CFCl_2CF_2Cl$ and 0.60 mmoles of unreacted dioxole. The trap at −196° C. contained 3.27 moles of unreacted $C_2F_4$. After distillation of the solvent and of the unreacted monomers and stripping of the polymer under vacuum at 120° C. for 3 hours, 1.830 g of polymer were isolated. The weight balance determined by g.l.c. of the traps containing the unreacted monomers allowed to calculate the molar percentage of dioxole in the polymer which resulted to be 3.3%.

The melting point was determined by DSC: the polymer melted at 296.7° C. with a melting ΔH of 7.5 cal/g; the Thermal Gravimetric Analysis (TGA) showed a weight loss of 2% at 457° C. and of 10% at 537° C. The cristallinity percentage, calculated from the melting ΔH, was 38%. The polymer was compression moulded (at 330° C., 122 arm) into a transparent and strong film.

EXAMPLE 11

Amorphous copolymer between TTD and $C_2F_4$.

In a 42 ml glass polymerization reactor, equipped with magnetic stirrer and inlet for feeding and discharging the reagents, 3 ml of $CCl_2FCF_2Cl$, 0.5 ml of a 1.3% solution of perfluoropropionylperoxide in $CCl_2FCF_2Cl$, 2.0 mmoles of 2,2,4-trifluoro- 5-trifluoromethoxy-1,3-dioxole and 10.0 mmoles of tetrafluoroethylene were introduced. The reactor was then brought to −196° C. and evacuated. After letting it warm up to room temperature, the reactor was heated to and kept at 40° C. for 8 hours under stirring. The raw reaction product appeared as a gelatinous mass. The reactor was brought to the temperature of liquid nitrogen, connected to a vacuum pump and maintained at a pressure of $10^{-3}$ mbar; then it was let warm up to room temperature, subdividing the evolved vapours by means of cool traps at −85° C., −120° C. and −196° C. The trap at −85° C. contained only $CFCl_2CF_2Cl$. The trap at −120° C. contained 3.50 mmoles of $CFCl_2CF_2Cl$ and 1.4 mmoles of unreacted dioxole. The trap at −196° C. contained 7.89 moles of unreacted $C_2F_4$. After distillation of the solvent and of the unreacted monomers and stripping of the polymer under vacuum at 120° C. for 3 hours, 0.335 g of white, solid polymer were isolated; the polymerization yield was 24%. The weight balance determined by g.l.c. of the traps containing the unreacted monomers allowed to calculate the molar percentage of dioxole in the polymer which resulted to be 22%. The glass transition temperature ($T_g$) of the polymer, determined by DSC, was 74° C.; the DSC track did not show any melting point: the polymer was amorphous. The Thermal Gravimetric Analysis (TGA) showed a weight loss of 2% at 410° C. and of 10% at 457° C.

EXAMPLE 12

Amorphous copolymer of TTD and $C_2F_4$.

In a 31 ml glass polymerization reactor, equipped with magnetic stirrer and inlet for feeding and discharging the reagents, 1.0 ml of $CCl_2FCF_2Cl$, 1.0 ml of a 1.3% solution of perfluoropropionylperoxide in $CCl_2FCF_2Cl$, 5.0 mmoles of 2,2,4-trifluoro- 5-trifluoromethoxy-1,3-dioxole and 10.0 mmoles of tetrafluoroethylene were introduced. The reactor was then brought to −196° C. and evacuated. After letting it warm up to room temperature, the reactor was heated to and kept at 40° C. for 8 hours under stirring. The raw reaction product appeared as a gelatinous mass. The reactor was brought to the temperature of liquid nitrogen, connected to a vacuum pump and maintained at a pressure of $10^{-3}$ mbar; then it was let warm up to room temperature, subdividing the evolved vapours by means of cool traps at −85° C., −120° C. and −196° C. The trap at −85° C. contained only $CFCl_2CF_2Cl$. The trap at −120° C. contained 2.40 mmoles of $CFCl_2CF_2Cl$ and 4.42 mmoles of unreacted dioxole. The trap at −196° C. contained 8.8 moles of unreacted $C_2F_4$. After distillation of the solvent and of the unreacted monomers and stripping of the polymer under vacuum at 120° C. for 3 hours, 0.240 g of white, solid polymer were isolated. The weight balance determined by g.l.c. of the traps containing the unreacted monomers allowed to calculate the molar percentage of dioxole in the polymer which resulted to be 32%. The glass transition temperature ($T_g$) of the polymer, determined by DSC, was 82.0° C.; the DSC track did not show any melting point: the polymer was amorphous. The Thermal Gravimetric Analysis (TGA) showed a weight loss of 2% at 381° C. and of 10% at 421° C.

EXAMPLE 13

TTD homopolymer

In a 18 ml glass polymerization reactor, equipped with magnetic stirrer and inlet for feeding and discharging the reagents, 1.0 ml of a 7.0% solution of perfluoropropionylperoxide in $CFCl_2CF_2Cl$ and 5.0 mmoles of 2,2,4-trifluoro- 5-trifluoromethoxy- 1,3-dioxole were introduced. The reactor was then brought to −196° C. and evacuated. After letting it warm up to room temperature, the reactor was heated to and kept at 60° C. for 8 hours under stirring. After distillation of the solvent and of the unreacted monomer, and stripping of the polymer under vacuum at 80° C. for 2 hours, 0.550 g of a liquid, viscous, transparent, soluble in $CFCl_2CF_2Cl$ polymer were isolated.

From $^{19}$F—NMR analysis, it appears that 6 repetitive TTD units were present on the average, while the endgroups were only —CF$_2$CF$_3$ units deriving from the initiator; the complete absence of —C(O)F groups was noticed; moreover, infrared analysis pointed out the complete absence of carbonyl products, showing that the TTD ring did not open during polymerization.

This result is of particular interest since it is known that, during polymerization, the fluorodioxoles of the prior art show a certain degree of dioxylic ring opening, with formation of carbonyl groups entering the polymeric molecule, with subsequent reduction of the thermal stability of the polymer. This phenomenon is described in International patent application WO 91/04251, page 26.

EXAMPLE 14

TTD homopolymer

In a 18 ml glass polymerization reactor, equipped with magnetic stirrer and inlet for feeding and discharging the reagents, 0.075 ml of a 7.0% solution of perfluoropropionylperoxide in CFCl$_2$CF$_2$Cl, and 5.0 mmoles of 2,2,4-trifluoro-5-trifluoromethoxy- 1,3-dioxole were introduced. The reactor was then brought to −196° C. and evacuated. After letting it warm up to room temperature, the reactor was kept at 25° C. for 48 hours under stirring. After distillation of the solvent and of the unreacted monomer, and stripping of the polymer under vacuum at 200° C. for 5 hours, 0.300 g of a white solid polymer in the form of powder were isolated. Infrared analysis showed complete absence of carbonyl products. The T$_g$ of the polymer, determined by DSC, was 162° C.; the DSC track did not show any melting point: the polymer was amorphous. The TGA showed a weight loss of 2% at 331° C. and of 10% at 381° C.

EXAMPLE 15

Amorphous copolymer of TTD and CF$_2$=CH$_2$.

In a 31 ml glass polymerization reactor, equipped with magnetic stirrer and inlet for feeding and discharging the reagents, 3.0 ml of CFCl$_2$CF$_2$Cl, 0.5 ml of a 1.3% solution of perfluoropropionylperoxide in CFCl$_2$CF$_2$Cl, 2.0 mmoles of 2,2,4-trifluoro- 5-trifluoromethoxy-1,3-dioxole and 10.0 mmoles of vinylidene fluoride were introduced. The reactor was then brought to −196° C. and evacuated. After letting it warm up to room temperature, the reactor was heated to and kept at 40° C. for 8 hours under stirring. The reactor was brought to the temperature of liquid nitrogen, connected to a vacuum pump and maintained at a pressure of 10$^{-5}$ mbar; then it was let warm up to room temperature, subdividing the evolved vapours by means of cool traps at −85° C., −120° C. and −196° C. The trap at −85° C. contained only CFCl$_2$CF$_2$Cl. The trap at −120° C. contained 4.20 mmoles of CFCl$_2$CF$_2$Cl and 1.3 mmoles of unreacted dioxole. The trap at −196° C. contained 8.7 moles of unreacted CF$_2$=CH$_2$. After distillation of the solvent and of the unreacted monomers and stripping of the polymer under vacuum at 120° C. for 3 hours, 0.230 g of polymer were isolated. The weight balance determined by g.l.c. of the traps containing the unreacted monomers allowed to calculate the molar percentage of dioxole in the polymer which resulted to be 34%. The T$_g$ of the polymer, determined by DSC, was 33.5° C.; the DSC track did not show any melting point: the polymer was amorphous. The TGA showed a weight loss of 2% at 355° C. and of 10% at 397° C.

EXAMPLE 16 (comparative)

Amorphous copolymer between PD and CF$_2$=CF$_2$.

In a 31 ml glass polymerization reactor, equipped with magnetic stirrer and inlet for feeding and discharging the reagents, 1.0 ml of CFCl$_2$CF$_2$Cl, ml of a 1.3% solution of perfluoropropionylperoxide in CFCl$_2$CF$_2$Cl, 4.0 mmoles of perfluorodioxole PD and 8.0 mmoles of tetrafluoroethylene were introduced. The reactor was then brought to −196° C. and evacuated. After letting it warm up to room temperature, the reactor was heated to and kept at 40° C. for 8 hours under stirring. After distillation of the solvent and of the unreacted monomers and stripping of the polymer under vacuum at 120° C. for 3 hours, 1.2 g of polymer were isolated. The weight balance determined by g.l.c. of the traps containing the unreacted monomers allowed to calculate the molar percentage of dioxole in the polymer which resulted to be 32%. The T$_g$ of the polymer, determined by DSC, was 90.0° C.; the DSC track showed a melting point at 314° C. and a melting ΔH of 3.8 cal/g: therefore, the obtained polymer was not completely amorphous.

We claim:

1. Thermoprocessable copolymers of tetrafluoroethylene having the following monomers:

(a) from 0.5 to 13% by weight of perfluoromethylvinylether;
    (b) from 0.05 to 3% by weight of one or more fluorinated dioxoles of formula:

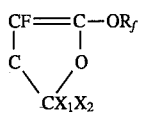

wherein: R$_f$ is a perfluoroalkyl radical having from 1 to 5 carbon atoms, and X$_1$ and X$_2$, equal or different from each other, are F or CF$_3$; and (c) tetrafluoroethylene, in such amount the the sum of the percentages of the various monomers is equal to 100% by weight.

2. The thermoprocessable copolymers of tetrafluoroethylene according to claim 1, wherein:

(a) the perfluoromethylvinylether is from 2 to 9% by weight; and
    (b) the fluorinated dioxoles are from 0.1 to 1.5% by weight.

3. The thermoprocessable copolymers of tetrafluoroethylene according to claim 1, wherein the fluorinated dioxole is 2,2,4-trifluoro-5-trifluoromethoxy-1,3-dioxole.

* * * * *